(12) United States Patent
Rapin et al.

(10) Patent No.: US 7,122,524 B2
(45) Date of Patent: *Oct. 17, 2006

(54) TRIPEPTIDES AND TRIPEPTIDE DERIVATIVES FOR THE TREATMENT OF POSTLESIONAL DISEASE OF THE NERVOUS SYSTEM

(75) Inventors: Jean Rapin, Paris (FR); Hans Klaus Witzmann, Egglkofen (DE); Jean-Marie Grumel, Tassin la Demi-Lune (FR); Jacques Gonella, Muttenz (CH)

(73) Assignee: Neurotell AG, Hergiswil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/635,805

(22) Filed: Aug. 5, 2003

(65) Prior Publication Data

US 2005/0080016 A1    Apr. 14, 2005

Related U.S. Application Data

(63) Continuation of application No. PCT/EP02/01183, filed on Feb. 5, 2002.

(51) Int. Cl.
*A61K 38/00* (2006.01)
*A61K 38/06* (2006.01)
*C07K 5/00* (2006.01)
*C07K 7/00* (2006.01)
*C07K 16/00* (2006.01)
*C07K 17/00* (2006.01)
*C07K 38/00* (2006.01)

(52) U.S. Cl. .......................................... 514/18; 530/331
(58) Field of Classification Search ................ 514/18; 530/330, 331, 338
See application file for complete search history.

(56) References Cited

U.S. PATENT DOCUMENTS

| | | | |
|---|---|---|---|
| 5,091,391 A * | 2/1992 | Aizenman et al. | 514/311 |
| 5,212,158 A | 5/1993 | Vandai | |
| 5,804,563 A * | 9/1998 | Still et al. | 514/26 |
| 5,840,838 A * | 11/1998 | Hensley et al. | 530/324 |
| 5,973,111 A | 10/1999 | Bemis et al. | |
| 6,080,848 A * | 6/2000 | Henrichwark et al. | 536/23.5 |
| 6,156,572 A | 12/2000 | Bellamkonda et al. | |
| 6,235,929 B1 | 5/2001 | Powers | |
| 6,645,518 B1 * | 11/2003 | Tedeschi et al. | 424/423 |
| 6,846,641 B1 * | 1/2005 | Wieloch et al. | 435/7.21 |

FOREIGN PATENT DOCUMENTS

| | | |
|---|---|---|
| EP | 0316218 A1 | 5/1989 |
| EP | 0445606 A1 * | 9/1991 |
| EP | 0446706 A2 | 9/1991 |
| EP | 0446706 A3 | 9/1991 |
| EP | 1018341 A | 7/2000 |
| EP | 1231279 A1 | 8/2002 |
| JP | 04-005240 A | 1/1992 |
| JP | 09040577 * | 2/1997 |
| JP | 09169797 * | 6/1997 |
| WO | WO 88/09604 A2 | 12/1988 |
| WO | WO 92/11850 A2 | 7/1992 |
| WO | WO92/13549 * | 8/1992 |
| WO | WO 96/41638 A1 | 12/1996 |
| WO | WO 98/14202 A1 | 4/1998 |
| WO | WO 01/28578 A2 | 4/2001 |
| WO | WO 01/28578 A3 | 4/2001 |
| WO | WO 01/34828 A1 | 5/2001 |
| WO | WO 01/68114 A1 | 9/2001 |
| WO | WO 02/062373 A2 | 8/2002 |
| WO | WO 02/062373 A3 | 8/2002 |
| WO | WO 02/062828 A2 | 8/2002 |
| WO | WO 02/062828 A3 | 8/2002 |

OTHER PUBLICATIONS

Kan. Current and future approaches to therapy of Alzheimer's disease. Eur J Med Chem 1992, vol. 27, pp. 565-570.*
del Zoppo et al. Trends and Future Developments in the Pharmacological Treatment of Acute Ischaemic Stroke. Drugs. Jul. 1977. vol. 1, pp. 9-38.*
Hofman et al. Atherosclerosis, apolipoprotein E, and prevalence of dementia and Alzheimer's disease in the Rotterdam Study, Lancet 1997, vol. 349, pp. 151-154.□□.*
Scientists uncover Alzheimer's clues. BBC News, Sunday Jun. 2000 (Accessed online May 3, 2005 at http://news.bbc.co.uk/1/hi/health/803297.stm) pp. 1-3.*
Faden, A.I., et al., "Effect of TRH analogs on neurologic recovery after experimental spinal trauma," *Neurology*, 35:1331-1334 (1985).

(Continued)

*Primary Examiner*—Cecilia J. Tsang
*Assistant Examiner*—Marcela M Cordero Garcia
(74) *Attorney, Agent, or Firm*—Madeline I. Johnston, Esq.; King & Spalding LLP

(57) ABSTRACT

The invention relates to the use of specific tripeptides for the treatment of postlesional diseases of ischemic, traumatic or toxic origin. The tripeptide derivatives satisfy the following formula (I): (see formula I as in paper form) wherein X represents OH, $(C_{1-5})$ alkoxy, $NH_2$, $NH-C_{1-5}$-alkyl, $N(C_{1-5}$ alkyl)$_2$; $R_1$ is a residue derived from one of the amino acids Phe, Tyr, Trp, Pro, which each may be optionally substituted with one or more $(C_{1-5})$ alkoxy groups, $(C_{1-5})$ alkyl groups or halogen atoms, as well as Ala, Val, Leu or Ile; $R_2$ is a residue derived from one of the amino acids Gly, Ala, Ile, Val, Ser, Thr, and Pro; $Y_1$ and $Y_2$ independently from each other represent H or $(C_{1-5})$ alkyl; $R_3$ and $R_4$ independently from each other represent H, OH, $(C_{1-5})$ alkyl or $(C_{1-5})$ alkoxy, provided that $R_3$ and $R_4$ are not both OH or $(C_{1-5})$ alkoxy; and $R_5$ represents H, OH, $(C_{1-5})$ alkyl or $(C_{1-5})$ alkoxy; or a pharmaceutically acceptable salt thereof.

6 Claims, 1 Drawing Sheet

OTHER PUBLICATIONS

Geschwind, M., et al., "Detection of apoptotic or necrotic death in neuronal cells by morphological, biochemical, and molecular analysis," in *Apoptosis Techniques and Protocols*, J. Poirier, ed., 1997, pp. 13-31.

Guiloff, R.J., "Thyrotropin releasing hormone and motorneurone disease", *Reviews in the Neurosciences*, 1:201-219 (1987).

Kurtz, A.F., "Praktische Diagnostik," in *Aktuelles Wissen Hoechst, Alzheimer-Patienten erkennen und behandeln*, Hoechst AG, publisher (Munich, Germany, 1995), 68-69. *With partial translation*.

Rapin, J.R., "Les nootropes: propriétés pharmacologiques du piracétam et indications thérapeutiques," *La Lettre du Pharmacologue*, 6(5):108-111 (1992). *With partial translation*.

Sarti, G., et al., "TRH-analogues: A possible treatment for symptoms of dementia in elderly patients?", *Archives of Gerontology and Geriatrics*, 12:173-177 (1991).

Szirtes, T., et al., "Synthesis of thyrotropin-releasing hormone analogues. 1. Complete dissociation of central nervous system effects from thyrotropin-releasing activity," *J. Med. Chem.* 27:741-745 (1984).

Beyer, H., and Walter, W., *Handbook of Organic Chemistry*, by S. Hirzel Verlag, Stuttgard (English translation of the 22$^{nd}$ edition of *Lehrbuch der Organischen Chemie*) (1996), pp. 827-838.

Blundell, T.L., et al., "Knowledge-based protein modelling and design", *Eur. J. Biochem.*, 172:513-520 (1988).

Chessebeuf, M., et al., "Rat liver epithelial cell cultures in a serum-free medium: primary cultures and derived cell lines expressing differentiated functions", *In Vitro*, 20(10):780-795 (1984).

Clark, M.C., et al., "Validation of the general purpose Tripos 5.2 force field", *J. Comp. Chem.*, 10(8):982-1012 (1999).

De Pooter, H., et al., "N-acylamino acids and peptides IV the synthesis of N-cinnamyl-, N-p.coumaryl- and N-caffeyl-glycine and -glycyl-L-phenylalanine", *Bull. Soc. Chim. Belg.*, 85(9):647-656 (1976). XP008015013.

Faden, A.I., et al., "Novel TRH analog improves motor and cognitive recovery after traumatic brain injury in rodents", *Amer. J. Physiology* 277(4, pt. 2):R1196-R1204 (1999), *Chem. Abstr.* 132:31033 XP002207513, XP008014976.

Faden, A.I., et al., "Structure-activity relationships of TRH analogs in rat spinal cord injury", *Brain Research*, 448:287-293 (1988). XP008015202.

Gasteiger, J., et al., "Iterative partial equalization of orbital electronegativity—a rapid access to atomic charges", *Tetrahedron*, 36:3219-3238 (1980).

Hagg, T., et al., "Delayed treatment with nerve growth factor reverses the apparent loss of cholinergic neurons after acute brain damage", *Exp. Neurol.*, 101:303-312 (1988).

Jones, D.T., et al., "A new approach to protein fold recognition", *Nature*, 358:86-89 (Jul. 1992).

Jones, D.T., "Protein secondary structure prediction based on position-specific scoring matrices", *J. Mol. Biol.*, 292(2):195-202 (1999).

Kansy, M., et al., "Physicochemical High Throughput Screening: Parallel Artificial Membrane Permeation Assay in the Description of Passive Absorption Processes", *J. Med. Chem.*, 41(7):1007-1010 (Mar. 26, 1998).

Khuebachova, M., et al., "Mapping the C terminal epitope of the Alzheimer's disease specific antibody MN423", *J. Immunol. Methods* (*Elsevier Amsterdam, NL*) 262(1-2):205-215 (2002).

Laskowski, R.A., et al., "PROCHECK: a program to check the stereochemical quality of protein structures", *J. Appl. Cryst.*, 26:283-291 (1993).

Le Poncin-Lafitte, M., et al., "Sound-avoidance conditioning and a mathematical approach to the description of acquisition performance", *Math. Biosciences*, 59:249-268 (1982).

Luco, J.M., "Prediction of the brain-blood distribution of a large set of drugs from structurally derived descriptors using partial least-squares (PLS) modeling", *J. Chem.. Inf. Comput. Sci.*, 39 (2):396-404 (1999).

Parnetti, L., et al., "Posatirelin for the treatment of late-onset Alzheimer's disease: a double-blind multicentre study vs citicoline and ascorbic acid", *Acta Neurol. Scand.* 92:135-140 (1995).

Varon, S., et al., "Nerve Growth Factor in CNS Repair", *J. Neurotrama*, 11(5) (1994).

Wang, R., et al., "SCORE: A new empirical method for estimating the binding affinity of a protein-ligand complex", *J. Mol. Model.*, 4:379-394 (1998).

Weiner, S.J., et al., "A new force field for molecular mechanical simulation of nucleic acids and proteins", *J. Am. Chem. Soc.*, 106:765-784 (1984).

Wiesman, C., et al., "Crystal structure of nerve growth factor in complex with the ligand-binding domain of the TrkA receptor", *Nature*, 401:184 (Sep. 9, 1999).

\* cited by examiner

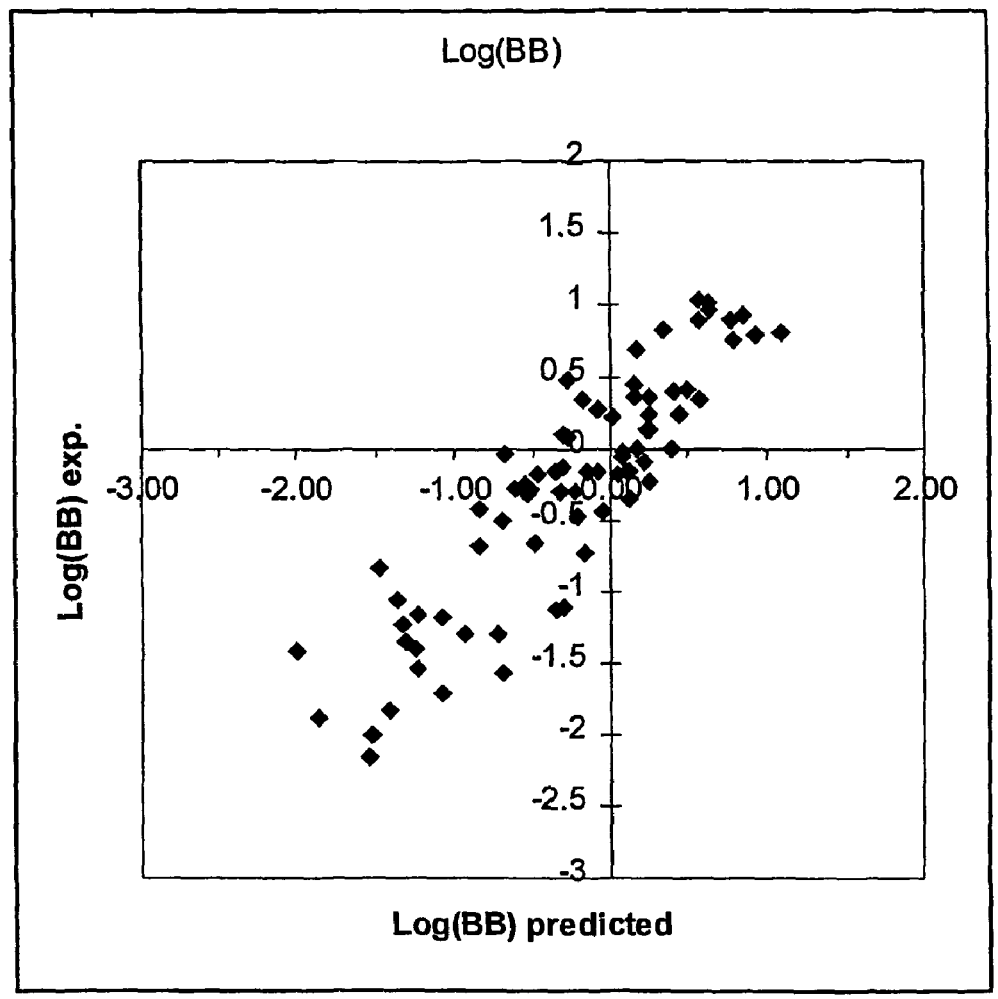
Fig. 1 Correlation between experimental and calculated brain-blood-distribution based on 15 descriptors.

TRIPEPTIDES AND TRIPEPTIDE DERIVATIVES FOR THE TREATMENT OF POSTLESIONAL DISEASE OF THE NERVOUS SYSTEM

This application is a continuation, under 35 U.S.C § 365(c), of the PCT patent application entitled "Tripeptides and Tripeptide Derivatives for the Treatment of Postlesional Diseases of the Nervous System," having International Application No. PCT/EP02/01183, International Filing Date of 5 Feb. 2002 (05.02.2002), and Priority Date of 5 Feb. 2001 (05.02.2001), which claims priority to German Patent Application No. 101 05 038.0, filed on Feb. 5, 2001, the disclosures of which are entirely incorporated herein by reference.

The invention relates to the use of tripeptides and tripeptide derivatives for the treatment of postlesional diseases of the nervous system, particularly those of necrotic origin such as e.g. ischemia, trauma or intoxication.

BACKGROUND ART

Ischemia of nerves or of nervous tissue is generally caused by vascular diseases, e.g. due to embolism or a thrombosis. The nerves of the central nervous system may be effected thereby, e.g. by a cerebral infarction. Ischemia ultimately leads to the necrotic death of the affected tissue.

A traumatic impact may also lead to such a death of the nerves. For example, spinal cord injuries and mechanical lesions of peripheral nerves are known. Moreover, environmental influences due to toxic substances, e.g. heavy metals, may result in a necrosis of nerves.

New therapeutic approaches for such nerve injuries comprise the administration of neurotrophic factors or of neurotrophines to which a significant influence on the survival, growth and differentiation of discrete neuronal populations is ascribed. The neurotrophine family includes nerve growth factor (NGF), brain derived neurotrophic factor (BDNF), neurotrophine-3 (NT-3), neurotrophine-4 (NT-4) and the CNTF-family (ciliary neurotrophic factor). Neurotrophines are small basic proteins with a molecular weight of 26 to 28 kDa. NGF is the best characterised member of the neurotrophine family which shows activity in many different tissues.

In the peripheral nervous system (PNS) NGF is critical to the development of sympathetic and certain sensory nerves. In the central nervous system (CNS), NGF serves a trophic role in the development and maintenance of cholinergic neurons of the basal forebrain. It also plays a role in adult CNS tissues in neuronal regeneration.

The use of neurotrophic factors for the treatment of postlesional neuronal diseases of e.g. traumatic, ischemic or toxic origin has not attained the expected success up to now.

Particularly in the case of the treatment of nerve injuries in the brain, neurotrophic factors are not suitable since they may not pass the blood-brain barrier and are thus not available for parenteral or enteral administration.

SUMMARY OF THE INVENTION

Therefore, it is the object underlying the present invention to provide substances which stimulate nerve growth and are thus suitable for the treatment of postlesional neuronal diseases as e.g. those of ischemic, traumatic or toxic origin.

This object of the present invention is solved by the use of compounds of the following formula (I):

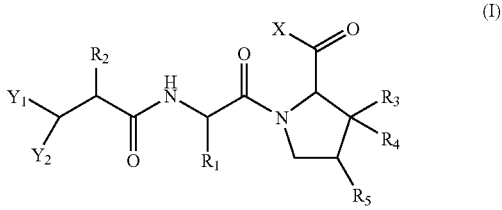

wherein X represents OH, $(C_{1-5})$ alkoxy, $NH_2$, $NH-C_{1-5}$-alkyl, $N(C_{1-5}$ alkyl$)_2$;

$R_1$ is a residue derived from one of the amino acids Phe, Tyr, Trp, and Pro, which each may be optionally substituted with one or more $(C_{1-5})$ alkoxy groups, $(C_{1-5})$ alkyl groups or halogen atoms, as well as Ala, Val, Leu or Ile;

$R_2$ is a residue derived from one of the amino acids Gly, Ala, Ile, Val, Ser, Thr, Leu and Pro;

$Y_1$ and $Y_2$ independently from each other represent H or $(C_{1-5})$ alkyl;

$R_3$ and $R_4$ independently from each other represent H, OH, $(C_{1-5})$ alkyl or $(C_{1-5})$ alkoxy, provided that $R_3$ and $R_4$ are not both OH or $(C_{1-5})$ alkoxy; and $R_5$ represents H, OH, $(C_{1-5})$ alkyl or $(C_{1-5})$ alkoxy;

or a pharmaceutically acceptable salt thereof;

for the preparation of a medicament useful in the treatment of postlesional diseases of ischemic, traumatic or toxic origin.

FIGURES

FIG. 1 shows the correlation of experimental and calculated values of the blood brain distribution.

DETAILED DESCRIPTION OF THE INVENTION

If not indicated otherwise, the amino acid residues may be present both in the D-form as well as the L-form, the L-form being preferred.

Preferred are compounds of the formula (I) in which $R_1$ is a residue derived from the amino acid Ile or one of the amino acids Phe, Tyr, Trp, which each may be optionally substituted with one or more $(C_{1-5})$ alkoxy groups, $(C_{1-5})$ alkyl groups or one or more halogen atoms, particularly a residue which is derived from Ile or Phe which is optionally substituted with one or more $(C_{1-5})$ alkoxy groups, one or more $(C_{1-5})$ alkyl groups or one or more halogen atoms.

In formula (I), X is preferably $(C_{1-5})$ alkoxy, $NH_2$, $NH-(C_{1-5})$ alkyl or $N(C_{1-5}$ alkyl$)_2$, more preferred are $NH_2$, $NH(C_{1-3})$ alkyl and $N(C_{1-3}$ alkyl$)_2$.

$R_2$ is preferably a residue derived from the amino acid Gly or Ile.

$R_3$ and $R_4$ preferably independently from each other represent H, $(C_{1-5})$ alkyl or $(C_{1-5})$ alkoxy, provided that $R_3$ and $R_4$ are not both OH or $(C_{1-5})$ alkoxy, more preferred are H, $(C_{1-3})$ alkyl or $(C_{1-3})$ alkoxy.

$R_5$ preferably represents H, $(C_{1-5})$ alkyl or $(C_{1-5})$ alkoxy, particularly preferred are H, $(C_{1-3})$ alkyl or $(C_{1-3})$ alkoxy.

$Y_1$ and $Y_2$ preferably independently from each other represent H or $(C_{1-3})$ alkyl.

For particularly preferred compounds of formula (I), $R_1$ is a residue which is derived from Phe which is optionally substituted with one or more ($C_{1-5}$) alkoxy groups, one or more ($C_{1-5}$) alkyl groups or one or more halogen atoms, or which is derived from the amino acid Ile, $R_2$ is a residue derived from the amino acid Gly or Ile, $R_3$, $R_4$ and $R_5$ represent a hydrogen atom, X is $NH_2$, NH—($C_{1-3}$) alkyl or N($C_{1-3}$ alkyl)$_2$, and $Y_1$ and $Y_2$ independently from each other represent H or ($C_{1-3}$) alkyl.

Most preferred compounds of formula (I) are glycyl-L-phenylalanyl-L-prolineamide, N,N-diethyl-isoleucyl-phenylalanyl-L-proline ethylamide, N,N-diethyl-isoleucyl-isoleucyl-prolineamide or a pharmaceutically acceptable salt thereof.

The abbreviations used for the amino acids (Phe for phenylalanine etc. as well as partially the one-letter-codes used below, such as F for phenylalanine) are known to the skilled person (see e.g. Beyer and Walter, Lehrbuch der Organischen Chemie, 21st edition, S. Hirzel Verlag Stuttgart 1988). Hence, Phe means phenylalanine, Gly glycine etc. The expression "a residue derived from the amino acid Phe" thus means a benzyl (—$CH_2$—$C_6H_5$) residue. Accordingly, "a residue derived from the amino acid Gly" means a hydrogen atom, "a residue derived from the amino acid Ala" a methyl group etc.

The compounds of formula (I) used according to the present invention are water soluble substances and are thus suitable for enteral or parenteral administration.

However, the compounds used according to the present invention are not all equally suitable for oral/enteral or parenteral administration. For example, whereas HCl-Gly-Phe-PrONH$_2$ is considered mainly for parenteral administration, N,N-Diethyl-Ile-Ile-ProNH$_2$ and N,N-Diethyl-Ile-Phe-ProNHEt are suitable for parenteral and particularly oral administration. The suitability of the compounds to be used according to the present invention for oral administration can be estimated using the so-called Parallel Artificial Membrane Permeation Assay which is described in more detail below. For oral administration, those compounds having values of more than 10, preferably more than 30, more preferably more than 45, as determined according to this assay, are preferred.

An essential prerequisite for the effectivity of the tripeptides and tripeptide derivatives used according to the present invention is their concentration in the CNS. Besides other factors, this is affected by the extent of the passage of the blood-brain barrier which may take place by active or passive transport. A so-called facilitated transport or transport via lipid rafts is considered as mechanisms. The balance of the transport is expressed independently from its type or mechanism by the blood-brain distribution coefficient (log BB). The higher this coefficient, the higher is the concentration in the CNS.

The definition and determination of the brain-blood distribution coefficient by molecular modelling in connection with QSAR (quantitative structure activity relationships) is described in more detail below. The blood-brain distribution coefficient of the compounds to be used according to the present invention is preferably −3,5 or higher, particularly preferred being one in the range of −3,0 and higher.

Furthermore, the substances of formula (I) used according to the present invention show a high affinity to tyrosine kinase receptors (TrkA, TrkB, and TrkC). Since the neurotrophic substance NGF is known to act via docking to these receptors, a high affinity to the receptors is a strong indication of the neurotrophic action of the compounds used according to the present invention. The docking constants (pKD) may be determined by molecular modelling tools, and a corresponding method is described in more detail below. The compounds used according to the present invention have preferably pKD-values of 5.5 or more, even more preferred are pKD-values of 7 or more.

The synthesis of the tripeptides and tripeptide derivatives used according to the present invention is not particularly limited and can be carried out according to known methods, preferably stereo-specific processes of peptide chemistry in which the L- or D-configuration of the respective amino acids or their derivatives is maintained. Various peptide syntheses are described in Beyer and Walter, Lehrbuch der Organischen Chemie, 21st edition, S. Hirzel Verlag Stuttgart 1988, pages 829–834. Preferred methods include the N-carboxylic acid anhydride method (NCA-method) and the method using mixed carboxylic acid anhydrides, as illustrated by the following reaction equations:

NCA-Method:
1. Boc-AA1-NCA+H-L-Pro-NH$_2$→BOC-AA1-L-Pro-NH$_2$
2. Boc-AA1-L-Pro-NH$_2$+TFA→TFA-H-AA1-L-Pro-NH$_2$
3. Boc-AA2-NCA+TFA-H-AA1-L-Pro-NH$_2$→HCl-H-AA2-L-AA1-Pro-NH$_2$
4. Boc-AA2-AA1-L-Pro-NH$_2$+HCl→HCl-H-AA2-AA1-L-Pro-NH$_2$ Mixed Carboxylic Acid Anhydride Synthesis:
1. Boc-AA1OH+Cl—COOCH$_2$(CH$_3$)$_2$→Boc-AA1-OCOO—CH$_2$CH(CH$_3$)$_2$
2. Boc-AA1-OCOOCH$_2$CH(CH$_3$)$_2$→Boc-AA1-L-Pro-NH$_2$
3. Boc-AA2-OH+Cl-COOCH$_2$CH(CH$_3$)$_2$→Boc-AA2-OCOOCH$_2$CH)CH$_3$)$_2$
4. Boc-AA2-OCOOCH$_2$CH(CH$_3$)$_2$+TFA-H-AA1-L-Pro-NH$_2$→Boc-AA2-AA1-L-Pro-NH$_2$
5. Boc-AA2-AA1-L-Pro-NH$_2$+HCl→HCl-H-AA2-AA1-L-Pro-NH$_2$ wherein AA1 and AA2 represent the middle and terminal amino acids (derived from $R_1$ or $R_2$) respectively, Boc represents a tert-butyloxycarbonyl residue, NCA represents N-carboxylic acid anhydride and TFA represents trifluoro acetic acid. The starting materials are commercially available.

When using amino acids having functional groups, such as e.g. serine, it is possible to protect these in a manner known to the skilled person.

Moreover, the tripeptides or tripeptide derivatives used according to the present invention may be synthesised in optionally modified Merryfield synthesis on a solid phase, preferably using fluoren-9-yl-methoxy-carbonyl protective groups (Fmoc residues) or Fmoc/tert-butyl (tBu) protected amino acids.

The reactions described above have yields of generally more than 90%, with respect to the individual reaction steps, and a total yield of more than 60%. The purity of the thus synthesised tripeptides and tripeptide derivatives is generally more than 98% and is thus sufficient for the use in pharmaceutical compositions. The structures of the tripeptides and tripeptide derivatives may be confirmed by mass spectroscopy (MS), high pressure liquid chromatography (HPLC), automated amino acid analysis (AAA), optical rotation (OR), and/or infrared and ultraviolet spectroscopy (IR, UV).

An administration in a dose of more than 5 mg per kilogram bodyweight per day is usually effective, particularly in multiple parenteral administration.

Due to their molecular structure these substances show a very low toxicity both in acute and chronic toxicity tests.

The smallest lethal dose (i.v.) in rats was 250 to 350 mg per kilogram bodyweight. Hence, the tested substances show a convenient therapeutical ratio which is a prerequisite for a therapeutical use in humans.

The tripeptides or tripeptide derivatives may be used for the production of pharmaceutical compositions which are suitable for administration in different ways, e.g. parenteral (intravenous, intramuscular, subcutane), via the respiratory tract (buccal, sublingual, nasal, bronchial), the transdermal route (percutane) and the enteral route (peroral). In the latter case, a suitable dosage is necessary to overcome the first pass effect.

The pharmaceutical compositions of the present invention further contain a pharmaceutically acceptable excipient, pharmaceutically acceptable diluents or adjuvants. Standard techniques may be used for their formulation, Standard techniques may be used for their formulation, as e.g. disclosed in Remington's Pharmaceutical Sciences, 20$^{th}$ edition Williams&Wilkins, PA, USA.

The administration form is selected depending on the administration route and comprises inter alia tablets, capsules, powders and solutions.

For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

A particularly preferred formulation for oral administration is a coated tablet containing 100 mg or 200 mg N,N diethyl-Ile-Ile-ProNH$_2$, silicon dioxide, magnesium stearate, Macrogol 400/600, Hypromellose (E404) titanium dioxide, and croscarmellose-Na.

For parenteral administration, sterile aqueous solutions are preferred. Suitable aqueous solvents include water, physiological saline solution, Hank solution und Ringer solution. Preferred is inter alia a physiological saline solution containing 20 g/l of the tripeptides or tripeptide derivatives, e.g. glycyl-L-phenylalanyl-L-prolineamide.

A particularly preferred formulation for parenteral administration is an ampul for injection containing 5 or 10 ml of injection solution for infusion comprising 100 mg or 200 mg of lyophilized HCl-Gly-Phe-ProNH$_2$, acetic acid, sodium acetate, and water for injection.

Particularly for treating spinal cord injuries and mechanical lesions of peripheral nerves, implantation of a material to which the compounds to be used according to the present invention have been immobilized, is a suitable method of ensuring guided nerve regrowth. Different methods of immobilization of peptides to a wide variety of materials are known (for references, see U.S. Pat. No. 6,156,572). According to the present invention, it is thus particularly preferred to immobilize the compounds of formula (I) on a biocompatible and possibly biodegradable material, such as hydrogels, preferably polysaccharide hydrogels, such as agarose, alginate or chitosan, or poly(lactide), polyethylene oxide, and hyaluronate. Immobilization methods of the peptides to these materials are known to the skilled person and include typical activation steps of hydroxyl groups for forming amide bonds, such as carbodiimide, such as EDC activation or the use of a bi-functional imidazole coupling agent, e.g. 1,1'-carbonyldiimidazole. Particularly useful immobilization matrices are disclosed in U.S. Pat. No. 6,156,572.

Moreover, the tripeptides to be used according to the present invention can be introduced into a peripheral nerve bridge which in turn is implanted into the transection lesion gap (see S. Varon, J. M. Conner, Nerve Growth Factor in CNS Repair, Journal of Neurotrauma, Vol. 11, No. 5, 1994).

The neuro-regenerative effect of the tripeptides or tripeptide derivatives used according to the present invention is surprising since peptides are usually subject to proteolytic degradation by endo- or exopeptidases and further metabolisation, so that it could not be expected that they reach and even pass the blood-brain barrier. The extent and the rate of this degradation is indicated by the half lifetime of the tripeptide or tripeptide derivative in plasma. It is known that the half-life period of tripeptides such as e.g. thyreoliberin (TRH) is very short. Therefore, it is surprising that the tripeptides and tripeptide derivatives used according to the present invention show an unexpectedly long half-life period ($\geq 24$ h). This long half-life period is a further prerequisite for a sufficient anti-neurodegenerative effect.

Moreover, in experiments with hepatocytes, it could be shown experimentally that the tripeptides and tripeptide derivatives of the present invention are only slowly metabolised in the liver. This result was confirmed by analysis of the plasma and of the added hepatocytes in which only the unaltered tripeptide was analyzed after an exposition of more than four hours.

The superior therapeutic properties of the tripeptides and tripeptide derivatives used according to the present invention will be further illustrated below using a neurite growth assay (sprouting assay). However, before describing these experiments in detail, the determination of the blood-brain distribution coefficient, the PAMPA assay, the determination of the TrK-docking constants, the determination of the half-life period and selected syntheses of the tripeptide derivatives used in the subsequent experiment is described.

Experimental Section

1. Determination of the Brain-blood Distribution Coefficient

As noted above, the blood-brain barrier generally presents an obstacle for water soluble substances impeding the use of many water soluble substances for the treatment of the CNS by common administration. However, it could be demonstrated that the tripeptides or tripeptide derivatives used according to the present invention show the capability of passing said blood-brain barrier. The blood-brain distribution of the tripeptides and tripeptide derivatives used according to the present invention may be quantified as follows.

The so-called QSAR (quantitative structure activity relationship) technique is an established technique for the quantification of specific physicochemical or pharmacological properties of chemical compounds. This technique generally comprises the determination of a linear correlation between a specific experimental property of the compounds (such as e.g. the brain-blood distribution coefficient (BB)) with calculated structural parameters A, B, C etc. by modulation of the so-called descriptors (X1, X2, etc.), generally resulting in an equation of the following form:

$$\text{Log } BB = (X1 \times A) + (X2 \times B) + (X3 \times C) + \ldots + \text{constant}$$

With the thus obtained descriptors it is then possible to calculate the respective experimental properties, such as e.g. the brain-blood distribution coefficient, of compounds for which no experimental data is available. Accordingly, the brain-blood distribution is determined as follows according to the present invention.

On the basis of experimental data of 75 compounds (see Luco, J. M., J. Chem. Inf. Comput. Sci. (1999), 39, 396–404) and specific parameters, as explained in the following, a linear correlation between calculated and experimental values could be obtained.

The compounds were constructed using the molecular modelling programme package SYBYL (Tripos Associates Inc., 1699 S. Henley Road, Suite 303, St. Louis, Mo. 63144, USA). To determine low energy conformations of the compounds for a selected set (A-F-P, A-dF-P, A-F-dP, A-dF-dP) a random search was performed. All dehedral angles, except those of the peptide bond, were considered flexible. The backbone conformations of the structures with the lowest energy were taken as the starting conformation for all compounds.

All manually constructed compounds were energetically minimised using the Tripos force fields (see Clark, M., Kramer, III, R. D. and van Optenbosch, N. (1989), J. Comp. Chem. 10, 982–991) with Gasteiger (PEOE) partial charges (Gasteiger, J., Marsili; M. (1980; Tetrahedron 36, 3219–3238)) and a distant-dependent dielectric constant of 4.

The molecular graphics programme MOE (Chemical Computing Group Inc., Montreal, Canada, http://www.chemcomp.com) allows the calculation of a widely applicable set of descriptors depending only on the connectivity of the compounds and the atom types (types in the sense of force field parameters) (see Labute on the home page cited above). All descriptors used herein include a simple approximation of the van der Walls surface of the compounds. For the test set of 1947 organic compounds, a high correlation ($r^2=0,9666$) resulted between the exact van der Walls surface and the 2D approximation. The first set of 14 parameters (PEOE-VSA) considered the charge distribution (PEOE) of the molecule using uniform interval boundaries. A second set of 10 descriptors (SlogP-VSA) describes the log (P) of the compounds and a third set of 8 (SMR-VSA) depend on molecular polarisability.

The values of all 32 descriptors described above were calculated for each of the 75 compounds (see Lucco, J. M., J. Chem. Inf. Comput. SCI. (1999), 39, 396–404) in order to find a correlation to the experimental brain-blood distribution. A principal components' regression has been performed to estimate a linear model of Log (BB) as a function of the descriptors. In the first calculation it appeared that 8 descriptors could be neglected due to very low contribution. After the second run without these 8, a further 9 descriptors with contributions less than 0.1 appeared. Finally, based on the calculations of 70 compounds (5 obvious outliers were removed) using the remaining 15 descriptors, a relatively good linear, as well as cross-validated (leave-one-out) correlation resulted. This correlation is graphically represented in FIG. 1 (in this graphic: used components: 15; condition number 663.7658; root mean square error (RMSE): 0,20126; correlation coefficient (R2): 0,03240; cross-validated R2: 0,88321).

Log (BB) is defined as follows:

LOG (BB)=Log (concentration in the brain)/(concentration in blood).

The descriptors obtained by this correlation could then be used for the calculation of the blood-brain distribution of the tripeptides and tripeptide derivatives of the present invention.

Inter alia, the following values were obtained which relate to the forms present in the physiological pH range:

| $A_1$ and $A_1$ derivates | $A_2$ and $A_2$ derivates | $A_3$ and $A_3$ derivates | brain-blood distribution coefficient |
|---|---|---|---|
| G | F | POH | −4.9 |
| G | F | $PNH_2$ | −3.3 |
| G | F | $PN(Et)_2$ | −3.3 |
| G | F | POEt | −2.8 |
| L | F | $PNH_2$ | −2.0 |
| G | D-F | $PNH_2$ | −3.3 |
| G | F | D-$PNH_2$ | −3.3 |
| A | P | $PNH_2$ | −3.1 |
| A | P | 3,3-di-Me-$PNH_2$ | −2.3 |
| I | P | 3,3-di-Me-$PNH^2$ | −2.1 |
| $N(Et)_2$-G | I | $PNH_2$ | −2.0 |
| $N(Et)_2$-I | I | $PNH_2$ | −1.6 |
| I | I | $PNH_2$ | −2.6 |
| I | S | $PNH_2$ | −3.5 |
| I | 3,4,5-tri-MeO—F | $PNH_2$ | −3.5 |
| I | 3,4-di-Me—F | $PNH_2$ | −2.7 |
| G | W | $PNH_2$ | −3.8 |
| G | Y | $PNH_2$ | −3.9 |

$A_1$: aliphatic amino acids including substitution at the amino group, corresponding to formula (I) $Y_1Y_2N$—$CR_2H$—CO—.
$A_2$: aromatic amino acids including substitution on the phenyl ring as well as aliphatic amino acids, according to formula (I) —NH—$CHR_1$—CO—.
$A_3$: proline and derivatives
D: dextro rotatory The following conclusions may be drawn from these calculations:
(a) The use of prolineamide, proline(diethyl)amide and the prolinemethylesters instead of the free acid of proline is preferred with regard to the passage of the blood-brain barrier.
(b) Among the structural units of $A_2$ (corresponding to R1), the aromatic amino acid F and alkyl derivatives thereof as well as isoleucine (I) are preferred.
(c) Among the structural units $A_1$ (corresponding to R2), the aliphatic amino acid I as well as the substitution of the amino group of G and I with 2 ethyl groups are particularly preferred.
(d) The optical chirality of the amino acid units does apparently not play a role at least for the passive passage of the blood-brain barrier.

2. Gastrointestinal Absorption

The absorption of an orally administered drug is determined by its ability to cross the gastrointestinal barrier. The Parallel Artificial Membrane Permeation Assay system (PAMPA) is a simple and fast method for the prediction of gastrointestinal drug absorption. Drug permeation of biological cell layers is mainly related to passive diffusion processes. The PAMPA method measures the permeation of potential new drugs across an artificial membrane by passive diffusion and allows a classification into low, medium and high absorbers.

The procedure according to the Parallel Artificial Membrane Permeation Assay described by Kansy et al. was used (Kansy M., Senner F., Gobernator K., Physicochemical High Throughput Screening: Parallel Artificial Membrane Permeation Assay in the Description of Passive Absorption Processes, J. Med. Chem., 1998, 41(7), 1007–1010). The artificial membrane was built up by pipetting a solution of lecithine in organic solvent on a supporting filter material in 96-well plates.

For all test compounds, stock solutions of 5 mM were prepared in ethanol. They were then diluted in Tris-buffer (0.05M, pH 7,4) to a final concentration of 500 μM. Permeation rates of all test compounds were measured in triplicate or quadruplicate. Diffusion time across the artificial membrane was 16 h. For all compounds reference values without phospholipid layer were individually determined. Concentrations in the acceptor compartments were measured by UV difference spectroscopy using a microtiter plate reader. Spectramax Plus[384] from Molecular Devices. For each compound the λmax values were determined in a previous run and measurements were performed at this wavelength. The permeation rates are expressed as flux rates, which are calculated according to the following formula: flux (%)=OD (test well)/OD (control well)×100. As internal standards, 3 drugs with known flux rates for low, medium and high permeation were included in the test plate: Bretylium, Hydrocortisone and Coumarin. After the permeation experiment, an integrity check of the membrane was performed to examine whether the test compounds injured the artificial membrane by a toxic or unspecific effect, and therefore constituting a false positive result. Lucifer Yellow, a non-permeating dye, has been applied to each well postexperimentally and the concentration of the marker measured in a Wallac Victor[2] 1420 Multilabel Counter. Wells, in which the concentration of Lucifer Yellow exceeded 1% of the amount detected in the control wells (without artificial membrane) were discarded. In the present experiment only one well (for the reference compound Bretylium) exceeded this limit and was therefore not taken into account.

Table 1 shows the flux rates of the 7 test compounds and the 3 reference compounds.

| Compounds | Pampa Flux (%) Mean ± SEM | Number of wells |
|---|---|---|
| HCl-Gly-Phe-ProNH$_2$ | 0 | 4 |
| TRH | <10 | 4 |
| N,N-Diethyl-Ile-Ile-ProNH$_2$ | 47 ± 1 | 4 |
| N-Isopropyl-Ile-Ile-ProNH$_2$ | 35 ± 1 | 3 |
| N,N-Diethyl-Gly-Ile-ProNH$_2$ | 25 ± 0.5 | 3 |
| N,N-Diethyl-Ile-Phe-ProNHEt | 51 ± 6 | 4 |
| H-Gly-Phe-Pro-OH | 0 | 4 |
| Bretylium | 0 | 2 |
| Hydrocortisone | 55 ± 1 | 4 |
| Coumarin | 72 ± 2 | 4 |

The internal control constituted by 3 reference compounds, the flux rates of which have been measured several times by us and others (see Kansy et al. above), have shown no abnormalities and attest the good conditions in which the experiment was performed. Bretylium, an actively transported compound, which shows a low bioavailability in humans, exhibited a flux rate of 0% in this experiment as well. The flux rates for Hydrocortisone and Coumarin, published by Kansy et al. (see above) were 52 and 66%, respectively. These data are in very good accordance to the results we obtained in our experiment (Table 1).

The PAMPA Method Allows a Classification of Compounds into 3 Groups:

Low (flux rate<20%), medium (20%<flux rate<50%) and high (flux rate>50%) permeators. According to this classification, HCl-Gly-Phe-ProNH$_2$, as well as TRH and H-Gly-Phe-Pro-OH will be weakly absorbed compounds, N,N-Diethyl-Ile-Ile-ProNH$_2$, N-Isopropyl-Ile-Ile-ProNH$_2$, N,N-Diethyl-Gly-Ile-ProNH$_2$ and N,N-Diethyl-Ile-Phe-ProNHEt are predicted to be medium to highly absorbed compounds after peroral application.

Based on the results obtained in this study, the following ranking of the test compounds for the permeability of biological membranes can be made:

HCl-Gly-Phe-ProNH$_2$, H-Gly-Phe-Pro-OH<TRH, N,N-Diethyl-Gly-Ile-ProNH$_2$<N-Isopropyl-Ile-Ile-ProNH$_2$<N,N-Diethyl-Ile-Ile-ProNH$_2$<N,N-Diethyl-Ile-Phe-ProNHEt A limitation of the PAMPA permeation test system as it is described here, is the fact that it can only detect compounds, which are transported by the transcellular route. Compound, which prefer the paracellular or active route might give low flux rates despite a good absorption in humans after peroral application.

3. Determination of Docking Constants

Based on X-ray structure or models of dimer fragments of TrkA, TrkB and TrkC, docking studies of several compounds of formula (I) were performed. For all the arrangements of the ligands between both monomers their affinity constants (pKd=pKi) should be calculated by means of theoretical methods (see Wang, R.; Liu, L., Lai, L., Tang, Y., J. Mol. Model., 1998, 4, 379–394).

a) Modelling of the Dimer Arrangement of the Receptors

The basis for all the following investigations is the X-ray structure (pdb=1 www) of a TrkA fragment docked by NGF (see Wiesmann, C., Ultsch, M. H., Bass, S. H., De Vos, A. M., Nature 1999, 401, 184).

We suppose that the ligands may bind in a similar way as NGF to two monomers of TrkA, TrkB or TrkC. The higher the affinity of the ligands, the closer both monomers will be held together, which is considered as the main function for activity. Since NGF is much larger than the tripeptide derivatives, models have to be formed which allow binding of the rather small molecules. For this purpose the coordinates of NGF were removed from the X-ray structure and one monomer was moved manually close to van der Walls contact to the other monomer (using the molecular modelling package SYBYL (TRIPOS Associates Inc.). To find a relevant arrangement of both unoccupied monomers together molecular dynamics simulations (MD) using the AMBER-ALL-ATOM force field (see S. J. Weiner et al., J. Amer. Chem. Soc. 1984, 106, 765–784) at 150 K for 20000 fs were carried out. The resulting structure after this simulation was optimised to an energy gradient of 0.1 kcal/mol Å2. This structure was used as template to model the structures of TrkB and TrkC as well as for docking studies.

Models of the dimer arrangement of TrkB and .TrkC were generated by using the homology modelling tool COMPOSER (see Blundell, T. L., Carney, D., Gardner, S., Hayes, F., Howlin, B., Hubbard, T., Eur. J. Biochem. 1988, 172–513–20) of SYBYL and subsequent MD and energy minimisations. The resulting structures were checked for quality using PROCHECK (see Laskowski, R. A., MacArthur, M. W., Moss, D. S., Thornton, J. M., J. Appl. Cryst., 1993, 26, 283–91).

b) Docking Studies of the Ligands

The program GOLD [See Jones, D. T., J. Mol. Biol., 1999, 292(2), 195–202; Jones, D. T., Taylor, W. R., Thornton, J. M., Nature 1992, 358, 86–89)] was used for "automatic" docking of the ligands. To ensure optimal docking for each of the ligands to all three receptors, two slightly different binding sites were investigated. Using GOLD for each run 20 docking structures (altogether 40) were determined.

Since the protein structures are considered to be fixed, all 40 arrangements were optimised keeping only the back bone of the receptor fixed.

c) Determination of the Affinity Constants

For all protein-ligand complexes the interaction energies of the ligands with the receptors were calculated using the Tripos force field, the so-called fitness values using GOLD and the program SCORE [see. Wang et al, ibid] to determine pKd-values which correspond to pKi-values in case of enzyme inhibitor complexes (the higher the fitness or pKd values the higher is the affinity of the ligands). SCORE considers not only interaction energies but also salvation, desolvation and entropy effects in the docking arrangements.

The results are summarised in the following table showing the best pKd (pKi)-values for each of the ligands to a receptor. The table also shows the values of the brain blood distribution as determined above.

The highest affinity was predicted for Et2-IFP-NH-Et (pKi-value of 7.29 (about 100 nM) when binding to TrkA (by SCORE). Some hydrogen bonds can be detected, however, most important are hydrophobic interactions of both N-terminal ethyl groups as well as of the Ile side chain with three histidine residues and of the phenylalanine side chain with Phe327 of the receptor. For all the remaining ligands the affinity is about one order of magnitude less.

| Ligand | Receptor | pKd value | Log BB |
| --- | --- | --- | --- |
| HCl-Gly-Phe-ProNH$_2$ | TrkC | 6.15 | −3.3 |
| N,N-Diethyl-Ile-Ile-ProNH$_2$ | TrkB | 6.15 | −1.7 |
| N-Isopropyl-Ile-Ile-ProNH$_2$ | TrkA | 6.31 | −2.2 |
| N,N-Diethyl-Gly-Ile-ProNH$_2$ | TrkA | 5.44 | −2.0 |
| N,N-Diethyl-Ile-Phe-ProNHEt | TrkA | 7.29 | −2.4 |
| H-Gly-Phe-Pro-OH | TrkC | 5.58 | −4.9 |

4. Syntheses a) Synthesis of HCl-H-Gly-L-Phe-L-Pro-NH$_2$

Step 1: Boc-L-Phe-OH+H-L-Pro-NH$_2$→Boc-L-Phe-L-Pro-NH$_2$ 87.6 g Boc-L-Phe-OH was dissolved in a mixture of 50 ml dimethylformamide (DMF) and 300 ml 1,2-dimethoxyethane (DME) and cooled to −15° C. Subsequently, 37 ml N-methylmorpholine (NMM) (1 equivalent) was added at once and subsequently 45 ml isobutylchloroformate (IBCF) (1 equivalent) was added dropwise over 10 min. The mixture was then stirred for further 5 min at −15° C. 40 g TFA.H-L-Pro-NH$_2$ (1.06 equivalents) was subsequently added in portions over 5 min, and then 315 ml N,N-diisopropyl-N-ethylamine (DIEA) (1 equivalent) was added at once. The reaction mixture was reacted over night at room temperature and atmospheric pressure. Subsequently, the reaction mixture was concentrated in a rotatory evaporator equipped with a water aspirator and a dry ice/acetone trap, and the residue was taken in 1 l of ethylacetate followed by twelve washes with 80 ml 1N aqueous KHSO$_4$ solution, one wash with 80 ml brine, ten washes with 80 ml saturated aqueous NaHCO$_3$ solution, one wash with 80 ml brine in a 2 l separatory funnel. The subsequent drying was carried out over 50 g Na$_2$SO$_4$. After filtration through a sinter glass funnel (coarse porosity) was concentrated as described above. The residue of evaporation (dry foam) was then triturated in 1 l hexane, and a solid was collected on a sinter glass funnel (120 mm i.d.×120 mm, medium porosity). This was followed by drying in a desiccator over 12 hours at room temperature and a pressure of 0.1 to 1 mm Hg (vacuum oil pump, with dry ice/acetone trap). Thus, 92.8 g Boc-L-Phe-L-Pro-NH$_2$ was obtained (yield: 77.8%).

| Analytical data: | |
| --- | --- |
| molar mass (mass spectroscopy): | 317 g/mol |
| melting point: | 60° C. (decomposition) |
| purity (HPLC): | 95.2% |
| optical rotation [Na/20° C.]: | −23.9 |
| H$_2$O [KF]: | 1.84% |
| heavy metals: | 25.4 ppm |
| solvents: | 2.02 °/$_{\infty}$ |
| element analysis: | 64.0% C |
| | 7.4% H |
| | 11.4% N |
| | 17.0% O |

Step 2: Boc-L-Phe-L-Pro-NH$_2$→TFA.H-L-Phe-L-Pro-NH$_2$

Boc-L-Phe-L-Pro-NH$_2$ (180 g) obtained in step 1 were dissolved/suspended in 250 ml methylene chloride in a 2 l round-bottom flask, equipped with a magnetical stirrer. Then, 250 ml of trifluoro acetic acid was reacted with the solution at room temperature (15–25° C.) and atmospheric pressure for one hour. The reaction mixture was then precipitated in 5 l tert-butylmethyl ether (TBME) under stirring. The precipitate was collected on a sinter glass funnel and subsequently washed twice with 1.5 l diethyl ether and twice with 1 l hexane. The subsequent drying was carried as described above in step 1.

Step 3: Boc-Gly-OH+TFA.H-L-Phe-L-Pro-NH$_2$→Boc-Gly-L-Phe-L-Pro-NH$_2$ 44 g Boc-Gly-OH (1 equivalent) was dissolved in a mixture of 50 ml DMF and 300 ml DME and subsequently cooled to −15° C. 28 ml NMM (1 equivalent) was added at once, followed by the dropwise addition of 34 ml IBCF (1 equivalent) over 10 min. The mixture was stirred a further 5 min at −15° C. 94.5 g TFA.H-L-Phe-L-Pro-NH$_2$ (1.06 equivalents) were added in portions thereto over 5 min, followed by the addition of 44 ml DIEA (1 equivalent). The reaction mixture was reacted over night at room temperature and atmospheric pressure. Subsequently, the reaction mixture was concentrated in a rotatory evaporator, equipped with a water aspirator and a dry ice/acetone trap, and the residue was taken in 1.2 l ethyl acetate, followed by five washes with 80 ml 1N aqueous KHSO$_4$ solution, five washes with 80 ml saturated aqueous NaHCO$_3$ solution, and one wash with 80 ml brine in a 2 l separatory funnel. The subsequent drying was carried out over 50 g Na$_2$SO$_4$. After filtration through a sinter glass funnel (coarse porosity) concentration was carried out as described above. The residue of evaporation (sticky oil) was then triturated in a mixture of 1 l diethyl ether and 2 l hexane and a solid was collected on a sinter glass funnel (180 mm i.d.×180 mm, medium porosity). The subsequent drying was carried out in a desiccator over 12 hours at room temperature and a pressure of 0.1 to 1 mm Hg (vacuum oil pump, with dry ice/acetone trap). Accordingly, 100 g Boc-Gly-L-Phe-L-Pro-NH$_2$ was obtained (yield: 94.7%).

| Analytical data: | |
|---|---|
| molar mass (mass spectroscopy): | 418 g/mol |
| melting point: | 66° C. (decomposition) |
| purity (HPLC): | 98.6% |
| optical rotation [Na/20° C.]: | −27.9 |
| $H_2O$ [KF]: | 3.78% |
| heavy metals: | 40.2 ppm |
| solvents: | 1.8 ‰ |
| element analysis: | 61.2% C |
| | 7.5% H |
| | 12.8% N |
| | 18.4% O |

Step 4: Boc-Gly-L-Phe-L-Pro-$NH_2$→HCL.H-Gly-L-Phe-L-Pro-$NH_2$

Boc-Gly-L-Phe-L-Pro-$NH_2$ (149 g) obtained in step 3 were dissolved/suspended in 300 ml methylene chloride and then 300 ml 4N HCl/dioxane was added at once. The mixture was reacted for one hour at room temperature (15–25° C.) at atmospheric pressure in a 2 l round-bottom flask equipped with a magnetical stirrer. Subsequently, 1 l diethyl ether was added to the reaction mixture and the precipitate was collected on a sinter glass funnel. The precipitate was then washed twice with 1.5 l diethyl ether and dried as described in step 1.

| Analytical data: | |
|---|---|
| molar mass (mass spectroscopy): | 318 g/mol |
| melting point: | 93° C. (decomposition) |
| purity (HPLC): | 98.8% |
| optical rotation [Na/20° C.]: | −19.1 |
| $H_2O$ [KF]: | 2.79% |
| heavy metals: | 15.9 ppm |
| solvents: | 0.72 ‰ |
| element analysis: | 53.7% C |
| | 6.4% H |
| | 14.3% N |
| | 14.9% O | b) Synthesis of N,N-Diethyl-Ile-Phe-Pro-NH-Et

N,N-Diethyl-Ile-Phe-Pro-NH-Et was prepared by solid phase synthesis as follows:

| Step | Reaction | Reagent | Time | Temperature |
|---|---|---|---|---|
| 0 | H-R + Fmoc-Phe-OH → Fmoc-Phe-R (I) | B | 2.00 h | 20° C. |
| 1 | (I) → H-Phe-R (II) | A | 0.25 h | 20° C. |
| 2 | (II) + Boc-Ile-OH → Boc-Ile-Phe-R (III) | B | 12.00 h | 20° C. |
| 3 | (III) → H-Ile-Phe-Pro-NH—Et (IV) | C | 1.50 h | 20° C. |
| 4 | (IV) → Separation by HPLC (IV) | D | | 20° C. |
| 5 | (IV) → N,N-Diethyl-Ile-Phe-Pro-NH—Et (V) | DMF, ethylbromide | | |
| 6 | (V) → Separation by HPLC (V) | D | | 20° C. |
| 7 | (V) → Lyophilisation (V) | | | 20° C. |
| 8 | (V) → Formation of Acetate (VI) | E | | 20° C. |
| 9 | (VI) → Lyophilisation (VII) store at −20° C. | | | −20° C. |

H-R: H-Pro-(SASRIN)-N—Et (proprietory of Bachem AG, CH; on polystyrene basis)
A: 20% Piperidine in DMF
B: DCCl/HOBt/DMF
C: 95% TFA, thereafter evaporation
D: RP-HPLC on C18, System: 0.1% TFA/Acetonitrile
E: anion exchanger in the acetate form, elution with water

| Analytical data: | |
|---|---|
| Appearance: | Yellowish product |
| Solubility: | 1 mg/ml in 5% acetic acid (clear, colorless solution) |
| Amino Acid Analysis: | Pro 1.00 (1) |
| | Phe 0.03 (1) |
| | Ile 0.01 (1) |
| | N, N diethyl-Ile cannot be determined; Ile-Phe bond incomplete hydrolysis |
| ESI-MS: | m = 458.5 u (average mass) |
| Purity (HPLC): | >95% |
| Water content: | 3.9% | c) Synthesis of N,N-Diethyl-Ile-Ile-Pro-NH-Et

N,N-Diethyl-Ile-Ile-Pro-NH-Et was prepared by solid phase synthesis as follows:

| Step | Reaction | Reagent | Time | Temperature |
|---|---|---|---|---|
| 0 | Fmoc-R → H-R (I) | A | 0.25 h | 20° C. |
| 1 | (I) + Fmoc-Ile-Pro-OH → Fmoc-Ile-Pro-R (II) | B | 1.25 h | 20° C. |
| 2 | (II) → H-Ile-Pro-R (III) | A | 0.25 h | 20° C. |
| 3 | (III) + Fmoc-Ile--OH → Fmoc-Ile-Ile-Pro-R (IV) | B | 1.50 h | 20° C. |
| 4 | (IV) → H-Ile-Ile-Pro-R (V) | A | 0.25 h | 20° C. |
| 5 | (V) → H-Ile-Ile-Pro-$NH_2$ (VI) + HO-R | C | 1.50 h | 20° C. |
| 6 | (VI) → N,N-Diethyl-Ile-Ile-Pro-$NH_2$ (VII) | DMF, ethylbromide | | |
| 7 | (VII) → Separation by HPLC (VII) | D | | 20° C. |
| 8 | (VII) → Lyophilisation (VII) | | | 20° C. |
| 9 | (VII) → Formation of Acetate (VIII) | E | | 20° C. |
| 10 | (VIII) → Lyophilisation (VIII) store at −20° C. | | | −20° C. |

Fmoc-R = Fmoc-Ramage-Resin (D-2200)
Fmoc-Ile-Pro-OH (B-2135), Fmoc-Ile-OH (B-1340)
A = 20% Piperidine in DMF
B = TBTU/DIPEA/DMF
C = 95% TFA, thereafter precipitation with IPE
D = RP-HPLC on $C_{18}$, System: 0.1% TFA/Acetonitrile
E = Anion Exchanger in the acetate form, Elution with $H_2O$

| Analytical data: | |
|---|---|
| Appearance: | Yellowish product |
| Solubility: | 1 mg/ml in water (clear, colorless solution) |
| Amino Acid Analysis: | Pro 1.00 (1) |
| | Ile 0.03 (1) |
| | N, N-diethyl-Ile cannot be determined; |
| | Ile-Ile bond incomplete hydrolysis |
| ESI-MS: | m = 396.5 u (average mass) |
| Purity (HPLC): | >96% |
| Water content: | 2.0% |

5. Determination of Metabolic Stability

Isolation and Culture of Rat Hepatocytes

Hepatocytes from adult male Wistar rats (IFFA Credo, L'Arbresle, France) were isolated by an in situ liver perfusion using collagenase (purchased from Sigma (St. Louis, Mo., U.S.A), according to a procedure described by Seglen (Preparation of isolated rat liver cell, Methods Cell Biol. 13, 29–83, 1976) and modified by Williams et al. (Rat hepatocyte primary culture. III. Improved dissociation and attachment techniques and the enhancement of survival by culture medium, in vitro 13: 809–817, 1977). After estimation of cell viability by the peripheral refractoriness of intact cells in phase contrast microscopy and the trypan blue test, freshly isolated hepatocytes were washed in basal William's medium E (WME) supplemented with 10% (v/v) fetal calf serum, 70 µM cortisol, 2 mM L-glutamine, 10 mM HEPES buffer, and 4 mM NaOH. They were then plated at a density of $0.5 \times 10^6$ cells per 50 mm plastic cell culture dishes in the medium described previously for cell attachment for 6 hours at 37° C. Subsequently, hepatocytes were washed three times in serum- and cholesterol-free medium (SF-WME) containing 4 g/l bovine albumin fraction V (Sigma) as transporter for 7.8 µM of a mixture of free fatty acids (Cheesebeuf M and Padieu P, expression of major liver metabolic function in long-term serum-free rat liver epithelial cell lines. In vitro 20: 780–795, 1984), and then were transferred to the SF-WME supplemented with the various tripeptides of formula (I). For each group of experiments, hepatocytes from three or four livers were used.

Statistics

Significances are calculated using Student's t-test. Values are expressed as mean±SD.

Analyses of the Tripeptides in Hepatocytes:

Method: (Hepatocytes in suspension)

Plasma sample: Precipitation with trichloracetic acid.

Centrifugation and aliquot of supernatant to HPLC.

Ion exchange column: Nucleosil C18 (250×4,6 mm).

Buffer TEAP 0,1%/CH$_3$CN, 1 ml/min

Readings at 210 nm.

Testing Conditions of the Tripeptides

20 µg/24 h/10$^6$ cells

10$^6$ cells/ml

Reduce substance to 10 µg/ml and 1,0 µg/ml.

Each substance of each concentration will be analysed 10 times during 24 h (1 h, 2 h, 4 h, 6 h, 8 h, 10 h, 12 h, 16 h, 20 h, 24 h).

Results

The following half-life values were obtained:

| Tripeptide | T½ (h) |
|---|---|
| N,N-Diethyl-Ile-Ile-ProNH$_2$ | 3.4 |
| N-Isopropyl-Ile-Ile-ProNH$_2$ | 2.6 |
| N,N-Diethyl-Gly-Ile-ProNH$_2$ | 2.8 |
| N,N-Diethyl-Ile-Phe-ProNHEt | 4.5 |
| H-Gly-Phe-Pro-OH | 0–1 |

6. Sprouting Assay

The sprouting of nerve cells is determined by the length of the dendrites. According to the present invention, the influence of the substances used according to the present invention on the sprouting is studied in an in vivo assay.

The septum of the hippocampus of 10 rats was destroyed (see Hagg et al; Exp. Neurol., 101, 303–312). 21 days after the impairment of the hippocampus was unambiguous, as confirmed by a behavioural test, the rats were divided into two groups of 5 rats each. 20 mg/per kg bodyweight per day of the substance used according to the present invention (GFPNH$_2$) was administered to the test group of 5 rats over at least 15 days.

After administration, the animals were killed, and the cholinergic nerve ends were observed by a CAT (choline-acetyl-transferase) immunofluorescence assay under a fluorescence microscope. The length of the dendrites was measured thereby.

In the rats of the control group, a change of the dendrite length of up to 2 µm was observed. On the other hand, the administration of the substance used according to the present invention resulted in an increase of the dendrite length of up to 8 to 10 µm in the test group. Hence, GFPNH$_2$ is a growth factor resulting in the growth of dendrites.

The invention claimed is:

1. A method for the treatment of a postlesional neuronal disease due to ischemia or traumatic impact, which is characterized by nerve cell necrosis, comprising administering an effective amount of a compound of formula (I) to a human patient in need thereof:

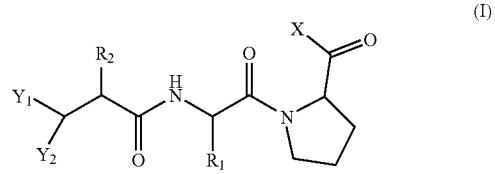

wherein X represents NH$_2$, NH-C$_{1-3}$-alkyl, or N(C$_{1-3}$ alkyl)$_2$;

R$_1$ is a residue derived from the amino acid Phe which may be optionally substituted with one or more methyl groups or one or more halogen atoms; or is a residue derived from the amino acid Ile;

R$_2$ is a residue derived from one of the amino acids Gly or Ile;

Y$_1$ and Y$_2$ independently from each other represent H or (C$_{1-3}$) alkyl;

or a pharmaceutically acceptable salt thereof.

2. The method according to claim 1, wherein X represents NH-$C_{1-3}$-alkyl, or N($C_{1-3}$ alkyl)$_2$.

3. The method according to claim 1, wherein $R_1$ is a residue derived from the amino acid Phe which may optionally be substituted with one or more methyl groups or one or more halogen atoms.

4. The method according to claim 3 wherein $R_1$ is a residue which is derived from Phe, which may optionally be substituted with one or more halogen atoms.

5. The method according to claim 1, wherein $R_2$ is a residue which is derived from the amino acid Gly.

6. The method according to claim 1, wherein the compound of formula (I) is glycyl-L-phenylalanyl-L-prolineamide, N,N-diethyl-isoleucyl-phenylalanyl-L-proline ethylamide, N,N-diethyl-isoleucyl-isoleucyl-prolineamide or a pharmaceutically acceptable salt thereof.

* * * * *